(12) United States Patent
Crnkovich et al.

(10) Patent No.: US 12,184,014 B2
(45) Date of Patent: *Dec. 31, 2024

(54) ELECTRICAL PLUG FOR A DIALYSIS MACHINE

(71) Applicant: Fresenius Medical Care Holdings, Inc., Waltham, MA (US)

(72) Inventors: Martin Joseph Crnkovich, Walnut Creek, CA (US); Colin Weaver, Pleasanton, CA (US); David Yuds, Hudson, NH (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/456,122

(22) Filed: Aug. 25, 2023

(65) Prior Publication Data

US 2023/0398272 A1 Dec. 14, 2023

Related U.S. Application Data

(60) Continuation of application No. 17/716,434, filed on Apr. 8, 2022, now Pat. No. 11,771,808, which is a
(Continued)

(51) Int. Cl.
*H01R 24/30* (2011.01)
*A61M 1/14* (2006.01)
(Continued)

(52) U.S. Cl.
CPC .............. *H01R 24/30* (2013.01); *A61M 1/14* (2013.01); *A61M 1/1656* (2013.01); *A61M 1/34* (2013.01);
(Continued)

(58) Field of Classification Search
CPC ........ A61M 1/14; A61M 1/1656; A61M 1/34; A61M 2205/505; A61M 2205/8262;
(Continued)

(56) References Cited

U.S. PATENT DOCUMENTS 3,922,659 A   11/1975   Dighe
4,025,139 A   5/1977    Martucci
(Continued)

FOREIGN PATENT DOCUMENTS

CN         204446745        7/2015
WO      WO 2012/170942     12/2012

OTHER PUBLICATIONS

International Preliminary Report on Patentability in Application No. PCT/US2018/012881, dated Jul. 16, 2019, 10 pages.
(Continued)

*Primary Examiner* — John Kim
(74) *Attorney, Agent, or Firm* — Fish & Richardson P.C.

(57) ABSTRACT

A dialysis machine comprising: a power supply for providing power to the dialysis machine, the power supply including a power supply cable that includes a first ground wire electrically connected to a first ground prong; and a hydraulics system for making dialysate, supplying the dialysate to a dialysate circuit, and draining spent dialysate from the dialysate circuit, the hydraulics system including a hydraulics grounding cable that includes a second ground wire electrically connected to a second ground prong.

19 Claims, 6 Drawing Sheets

Related U.S. Application Data continuation of application No. 16/686,920, filed on Nov. 18, 2019, now Pat. No. 11,303,075, which is a division of application No. 15/404,725, filed on Jan. 12, 2017, now Pat. No. 10,512,715.

(51) Int. Cl.

| | | |
|---|---|---|
| *A61M 1/16* | (2006.01) | |
| *A61M 1/34* | (2006.01) | |
| *H01R 13/02* | (2006.01) | |
| *H01R 13/633* | (2006.01) | |
| *H01R 13/652* | (2006.01) | |
| *H01R 24/76* | (2011.01) | |
| *H01R 24/78* | (2011.01) | |
| *H01R 31/02* | (2006.01) | |
| *H01R 31/06* | (2006.01) | |
| *H01R 103/00* | (2006.01) | |

(52) U.S. Cl.
CPC ....... *H01R 13/025* (2013.01); *H01R 13/6335* (2013.01); *H01R 13/652* (2013.01); *H01R 24/76* (2013.01); *H01R 24/78* (2013.01); *H01R 31/02* (2013.01); *H01R 31/06* (2013.01); *A61M 2205/505* (2013.01); *A61M 2205/8262* (2013.01); *A61M 2209/00* (2013.01); *H01R 2103/00* (2013.01); *H01R 2201/12* (2013.01)

(58) Field of Classification Search
CPC ............. A61M 2209/00; H01R 13/652; H01R 13/025; H01R 13/6335; H01R 2103/00; H01R 2201/12; H01R 24/30; H01R 24/76; H01R 24/78; H01R 31/02; H01R 31/06
See application file for complete search history.

(56) References Cited

U.S. PATENT DOCUMENTS

| | | | |
|---|---|---|---|
| 4,155,852 | A | 5/1979 | Anderson et al. |
| 4,190,047 | A | 2/1980 | Jacobsen et al. |
| 6,644,986 | B1 | 11/2003 | Wilker |
| 10,512,715 | B2 | 12/2019 | Crnkovich et al. |
| 2005/0211460 | A1 | 9/2005 | Draggie et al. |
| 2009/0008306 | A1 | 1/2009 | Cicchello et al. |
| 2014/0213962 | A1 | 7/2014 | Marterstock |
| 2015/0079820 | A1 | 3/2015 | Harris |

OTHER PUBLICATIONS

International Search Report and Written Opinion in International Application No. PCT/US2018/012881, dated Jul. 9, 2018, 17 pages.
Communication of a Notice of Opposition in European Appln. No. 18709142.6, dated Sep. 17, 2024, 91 pages (with machine translation).
Opposition, "Braun Avitum AG, 'Dialog+ Dialysis Machine: Instructions for Use SW 9.1x, IFU 38910363US, Rev. 2.15.00'," Exhibit E4b in European Appln. No. 18709142.6, dated May 2016, 284 pages.
Opposition, "Braun Avitum AG, 'Dialysegerät Dialog+: Gebrachsanweisung SW 9.1x, GBA 38910318DE; Rev. 2.17.00'," Exhibit E4 in European Appln. No. 18709142.6, dated Jul. 2013, 615 pages (with machine translation).
Opposition, "DIN 42801," Exhibit E13 in European Appln. No. 18709142.6, dated Apr. 1980, 4 pages (with English abstract).
Opposition, "DIN EN 60601-2-16 (VDE 0750-2-16)," Exhibit E11 in European Appln. No. 18709142.6, dated Feb. 2016, 80 pages (with English abstract).
Opposition, "DIN VDE 0100-710 (VDE 0100-710), " Exhibit E12 in European Appln. No. 18709142.6, dated Oct. 2012, 53 pages (with English abstract).
Opposition, "Elektrotechnik Automatisierung, 'Steckverbinder für den Potentialausgleich gemäß DIN 42801'," Exhibit E14 in European Appln. No. 18709142.6, dated Nov. 9, 2013, 3 pages (with English translation).
Opposition, "Geberth et al., 'Praxis der Dialyse: 2. Auflage'," Exhibit E6 in European Appln. No. 18709142.6, dated 2014, 416 pages (with English abstract).
Opposition, "Rechnung uber den Verkauf von zwei Dialysegeraten Dialog+ inkl. Zweier Gebrauchsanleitungen," Exhibit E4a in European Appln. No. 18709142.6, dated May 21, 2015, 4 pages (with machine translation).
Opposition, "Wikipedia, "AC power plugs and sockets"," Exhibit E9 in European Appln. No. 18709142.6, dated Dec. 17, 2016, 43 pages.
Opposition, "Wikipedia, 'Erdschleife'," Exhibit E15 in European Appln. No. 18709142.6, dated Dec. 6, 2016, 14 pages (with English translation).
Opposition, "Wikipedia, 'Potentialausgleich'," Exhibit E10 in European Appln. No. 18709142.6, dated Dec. 9, 2016, 7 pages (with English translation).
Opposition, "Wikipedia, 'Schuko'," Exhibit E8 in European Appln. No. 18709142.6, dated Jan. 10, 2017, 19 pages (with English translation).
Opposition, "Wikipedia, 'Steckverbinder'," Exhibit E16 in European Appln. No. 18709142.6, dated Jul. 24, 2016, 19 pages (with English translation).
Opposition, "WO 2004/108206," Exhibit E7 in European Appln. No. 18709142.6, dated Dec. 16, 2004, 45 pages.
Opposition, "WO 2017/064251," Exhibit E5 in European Appln. No. 18709142.6, dated Apr. 20, 2017, 37 pages.

ELECTRICAL PLUG FOR A DIALYSIS MACHINE

CROSS-REFERENCE TO RELATED APPLICATION

This application is a continuation application of and claims the benefit of priority under 35 U.S.C. § 120 to U.S. application Ser. No. 17/716,434, filed Apr. 8, 2022, now U.S. Pat. No. 11,771,808, which is a continuation of U.S. application Ser. No. 16/686,920, filed Nov. 18, 2019, now U.S. Pat. No. 11,303,075, which is a divisional of U.S. application Ser. No. 15/404,725, filed Jan. 12, 2017, now U.S. Pat. No. 10,512,715, the entire contents of which are hereby incorporated by reference.

TECHNICAL FIELD

This disclosure relates to an electrical plug for a dialysis machine.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

SUMMARY

In one aspect, a dialysis machine includes a power supply for providing power to the dialysis machine. The power supply includes a power supply cable that includes a first ground wire electrically connected to a first ground prong. The dialysis machine also includes a hydraulics system for making dialysate, supplying the dialysate to a dialysate circuit, and draining spent dialysate from the dialysate circuit. The hydraulics system includes a hydraulics grounding cable that includes a second ground wire electrically connected to a second ground prong.

Implementations can include one or more of the following features.

In some implementations, the first ground wire and the first ground prong form a first grounding connection, and the second ground wire and the second ground prong form a second grounding connection.

In some implementations, the first grounding connection is separate and distinct from the second grounding connection.

In some implementations, the power supply cable and the hydraulics grounding cable are connected to a combined plug that is configured to plug into an AC power outlet.

In some implementations, the combined plug includes a line prong that is electrically connected to a line wire of the power supply cable, a neutral prong that is electrically connected to a neutral wire of the power supply cable, and the first ground prong that is electrically connected to the first ground wire of the power supply cable. The combined plug also includes the second ground prong that is electrically connected to the second ground wire of the hydraulics grounding cable.

In some implementations, the first ground prong and the first ground wire are electrically isolated from the second ground prong and the second ground wire.

In some implementations, the first ground prong and the first ground wire are in electrical communication with the second ground prong and the second ground wire via a connection that occurs behind a wall plate of the AC power outlet when the combined plug is plugged into the AC power outlet.

In some implementations, the combined plug is a contiguous piece of material to which all prongs are connected.

In some implementations, the combined plug also includes non-conductive prongs for improving an integrity of a connection between the combined plug and the AC power outlet.

In some implementations, the combined plug includes a handle to facilitate simultaneous connection of the power supply cable and the hydraulics grounding cable to the AC power outlet.

In some implementations, the first ground wire and the second ground wire do not share a common insulation.

In some implementations, the dialysis machine complies with one or more requirements specified by a standards organization when the first grounding connection is connected to a first AC socket of an AC power outlet and the second grounding connection is connected to a second AC socket of the AC power outlet.

In some implementations, the standards organization is the International Electrotechnical Commission (IEC) and the one or more requirements are specified in IEC 60364-7-710.

In some implementations, the hydraulics grounding cable is configured to plug into a grounding socket of the dialysis machine.

In some implementations, the grounding socket is in electrical communication with a metal chassis of the hydraulics system.

In some implementations, the dialysis machine is a hemodialysis ("HD") machine.

In some implementations, the power supply cable and the hydraulics grounding cable electrically connect to the dialysis machine at separate locations at the housing of the dialysis machine.

In another aspect, a plug that is configured to plug into an AC power outlet includes a power supply cable that includes a first ground wire electrically connected to a first ground prong. The power supply cable is for providing power to a dialysis machine. The plug also includes a hydraulics grounding cable that includes a second ground wire electrically connected to a second ground prong. The hydraulics grounding cable is for providing a grounding connection to a hydraulics system of the dialysis machine. The plug also includes a handle for facilitating simultaneous connection of the power supply cable and the hydraulics grounding cable to an AC power outlet. The grounding connection of the hydraulics system is separate and distinct from the first ground wire and the first ground prong of the power supply cable.

Implementations can include one or more of the following features.

In some implementations, the first ground prong and the first ground wire are electrically isolated from the second ground prong and the second ground wire.

In some implementations, the first ground wire and the second ground wire do not share a common insulation.

In some implementations, the plug also includes an adapter that is configured to removably connect to and form an electrical connection with the power supply cable, removably connect to and form an electrical connection with the hydraulics grounding cable, and plug into the AC power outlet.

Implementations can include one or more of the following advantages.

In some implementations, providing a separate grounding connection for the hydraulics system allows the dialysis machine to meet requirements specified by a standards organization, such as the International Electrotechnical Commission (IEC), and in particular, to meet the requirements of IEC 60364-7-710 and/or IEC 60601-2-16. The separate grounding connection helps to ensure that the patient's safety is maintained by protecting the patient from leakage currents of an unacceptable magnitude.

In some implementations, the combined plug ensures that both grounding connections are concurrently made. For example, in implementations in which the power supply cable and the hydraulics grounding cable do not share a combined plug, an operator or technician may forget to plug the hydraulics grounding cable into the second AC socket. Forgetting to connect the hydraulics grounding cable may be more likely because the hemodialysis machine may require only the power supply cable to be connected in order to operate. In other words, the hemodialysis machine may be able to operate without the hydraulics grounding cable being connected. Therefore, including the second end of the power supply cable and the second end of the hydraulics grounding cable as a combined plug may ensure that both the first grounding connection and the second grounding connection are made simultaneously and/or maintained concurrently.

Other aspects, features, and advantages of the subject matter included herein will be apparent from the description and drawings, and from the claims.

DESCRIPTION OF DRAWINGS

Like reference symbols in the various drawings indicate like elements.

DETAILED DESCRIPTION

A medical device, such as a dialysis machine (e.g., a hemodialysis machine) may include multiple separate electrical grounding connections. For example, the dialysis machine may include a power supply that includes a first grounding connection (e.g., as part of an AC power plug) and a separate system (e.g., a hydraulics system) that includes a second grounding connection (e.g., a non-standard connection). The first grounding connection and the second grounding connection may include separate, distinct wires that each terminates at a separate grounding location. For example, the first grounding connection may terminate at a ground (e.g., earth ground) of a first AC socket and the second grounding connection may terminate at a ground (e.g., earth ground) of a second AC socket. The first and second AC sockets may be part of the same AC power outlet. Therefore, the two earth grounds may be electrically connected by wiring that resides behind a wall plate of the AC power outlet. In some implementations, while the two grounding connections may be provided as separate, distinct wires (e.g., which may be enclosed within separate cabling), the two grounding connections may be incorporated as a single (e.g., combined) plug to ensure that both grounding connections are made substantially simultaneously and/or maintained concurrently.

Figure 1A:
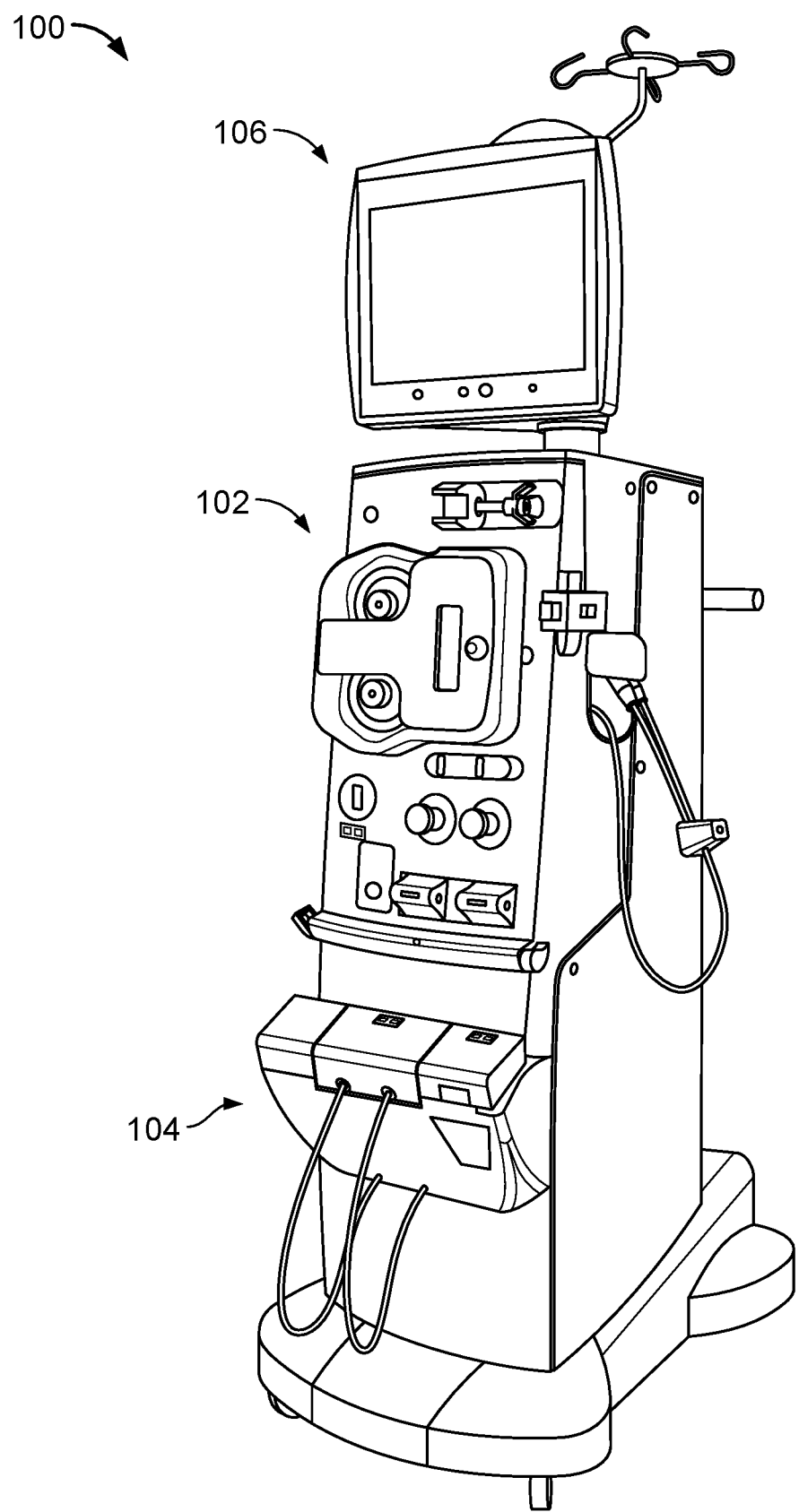
FIG. 1A is a front perspective view of a hemodialysis machine.

FIG. 1A shows a front perspective view of an example of a medical device such as a hemodialysis machine 100. The hemodialysis machine 100 includes, among other things, a blood circuit module 102 and a hydraulics system 104. In general, during hemodialysis, arterial and venous patient lines of the blood circuit module 102 are connected to a patient and blood is circulated through various blood lines and components, including a dialyzer. At the same time, dialysate is circulated through a dialysate circuit formed by the dialyzer and various other dialysate components and dialysate lines connected to the hemodialysis machine 100. Many of these dialysate components and dialysate lines are located inside the housing of the hemodialysis machine 100, and are thus not visible in FIG. 1A.

The dialysate passes through the dialyzer along with the blood. The blood and dialysate passing through the dialyzer are separated from one another by a semi-permeable structure (e.g., a semi-permeable membrane and/or semi-permeable microtubes) of the dialyzer. As a result of this arrangement, toxins are removed from the patient's blood and collected in the dialysate. The filtered blood exiting the dialyzer is returned to the patient. The dialysate that exits the dialyzer includes toxins removed from the blood and is commonly referred to as "spent dialysate." The spent dialysate is routed from the dialyzer to a drain. When ultrafiltration is performed during treatment, a combination of the spent dialysate and excess fluid drawn from the patient is carried to the drain via an ultrafiltration line.

The hemodialysis machine 100 includes a monitor in the form of a touch screen 106. The touch screen 106 allows an operator to input various treatment parameters to the hemodialysis machine 100 and to otherwise control the hemodialysis machine 100. In addition, the touch screen 106 serves as a display. The touch screen 106 functions to provide information to the patient and the operator of the hemodialysis machine 100. For example, the touch screen 106 may display information related to a dialysis treatment to be applied to the patient.

The hemodialysis machine 100 also includes a processing module that resides inside the machine and which is configured to communicate with the touch screen 106. The processing module is configured to receive data from the touch screen 106 and control the hemodialysis machine 100 based on the received data. For example, the processing module can adjust the operating parameters of the hemodialysis machine 100.

The components of the hemodialysis machine 100 that are responsible for making, balancing, supplying, and draining the dialysate are generally referred to as the hydraulics system 104. The hydraulics system 104 includes, among other things, the dialysate circuit (e.g., including the various dialysate lines, dialysate components, and the dialyzer) and a balancing chamber (e.g., where the volumes of fluid to and from the dialyzer are volumetrically balanced).

The hemodialysis machine 100 is generally powered by a power supply. The power supply may be configured to provide power to all components of the hemodialysis machine 100, including but not limited to the blood circuit module 102, the hydraulics system 104, and the touch screen 106. The power supply includes a grounding connection (e.g., as part of an AC power plug). However, one or more components and/or systems of the hemodialysis machine 100 may include its own grounding connection. For example, the hydraulics system 104 may include a grounding connection that is separate from the grounding connection of the power supply that is configured to separately ground the components that make up the hydraulics system 104. In this way, the grounding connection of the hydraulics system 104 provides a separate and distinct grounding connection for the hydraulics system 104 (e.g., as opposed to providing a second, redundant, ground connection for the power supply).

In some implementations, the separate grounding connection for the hydraulics system 104 may be included at least in part to comply with standards established by a standards organization. For example, the hemodialysis machine 100 may be configured and arranged to meet Class I regulations and/or to comply with requirements specified by the International Electrotechnical Commission (IEC), in particular, with IEC 60364-7-710.

IEC 60364-7-710 specifies that the following requirements must be observed by the hemodialysis machine 100 when it is connected to an AC power supply:
Power failures <20 ms;
A grounding system must be installed as prescribed;
A power socket with a protective earth connection is required;
The line cross-section and line lengths to the power socket must be dimensioned so as to ensure that the voltage tolerance and the function of the protective devices is always guaranteed (recommended line cross-section to the power socket: at least 3×1.5 mm² copper core for 220 V-240 V and at least 3×2.5 mm² copper core for voltages of less than 220 V);
Each electric circuit is protected from damage through fault conditions with an automatic, fast-acting circuit breaker (recommendation: 16 A at 220 V-240 V and 20 A at voltages lower than 220 V);
No more than one device per wall socket and electric circuit;
The use of power strips and extension cables is prohibited;
Residual-current devices (RCDs) which protect against dangerous shock currents in the event of fault conditions (recommendation: one RCD (fault current less than 30 mA) for each device (or socket)); and
Overvoltage/lightning protection in the main and emergency power supply networks.

In some implementations, the separate grounding connection for the hydraulics system 104 may be included at least in part due to a leakage current surpassing an acceptable limit. For example, IEC 60364-7-710 (or, e.g., another standard) may specify that patient leakage currents for type CF applied parts (e.g., parts that are in direct conductive contact with the heart or other applications as considered necessary) may not surpass 10 μA AC/DC for normal condition (e.g., no fault condition) and 50 μA AC/DC for single fault condition. Failure to provide the separate grounding connection may put the patient at risk (e.g., due to electric current of a dangerous magnitude running through the patient). If one or more of these conditions are not met by the hemodialysis machine 100, one option for alleviation may be the inclusions of the separate grounding connection for the hydraulics system 104.

In some implementations, the separate grounding connection for the hydraulics system 104 may be included at least in part to comply with requirements and/or standards imposed by a particular country. For example, the hemodialysis machine 100 may be able to satisfy the requirements imposed by a first country without including separate grounding connections, but the hemodialysis machine 100 may be required to include separate grounding connections in order to satisfy the requirements of a second country. By including separate grounding connections, the hemodialysis machine 100 may be sold worldwide (e.g., rather than providing different versions of the hemodialysis machine 100 to different countries).

Figure 1B:
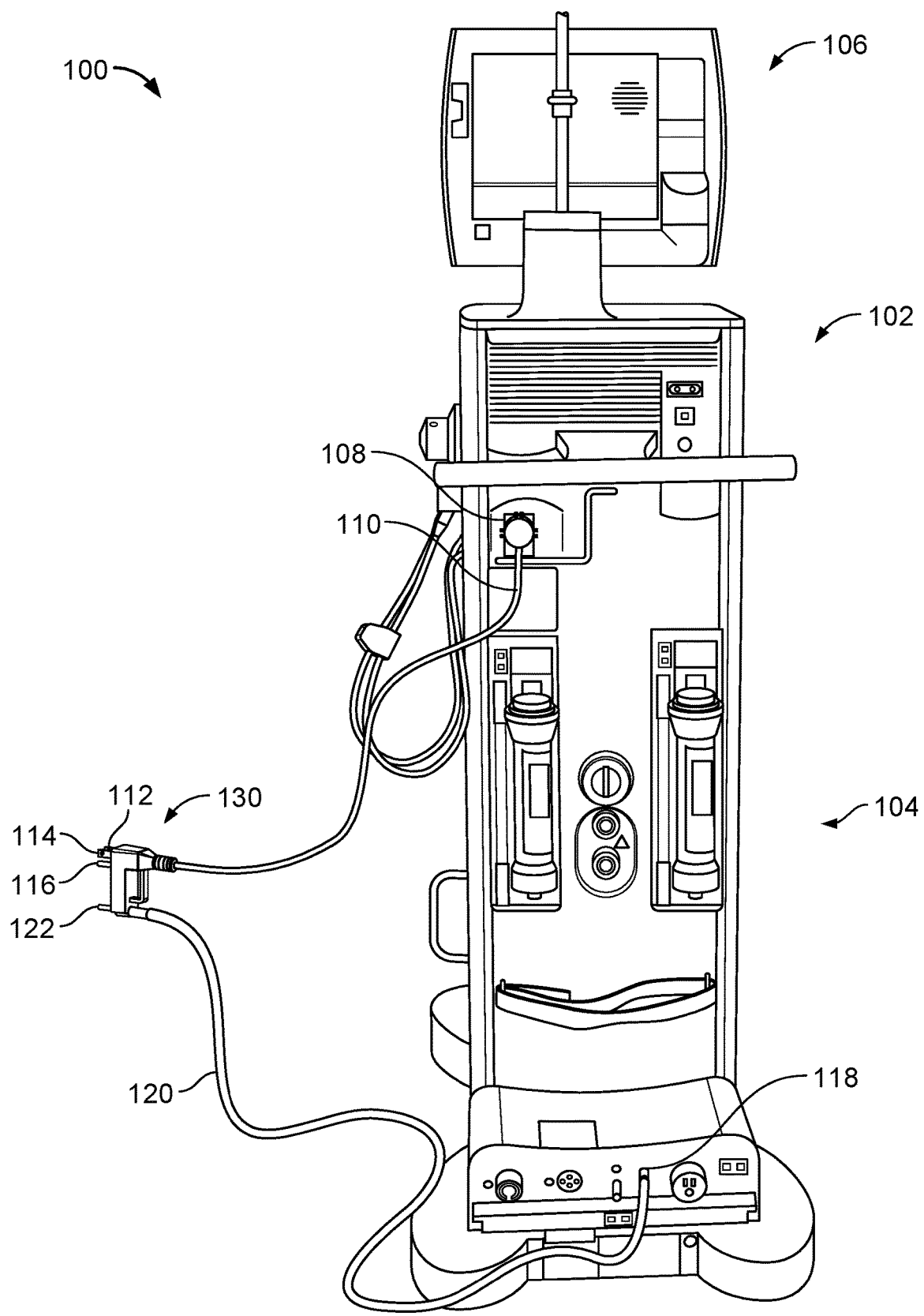
FIG. 1B is a back perspective view of the hemodialysis machine that shows two separate grounding connections.
Figure 2:
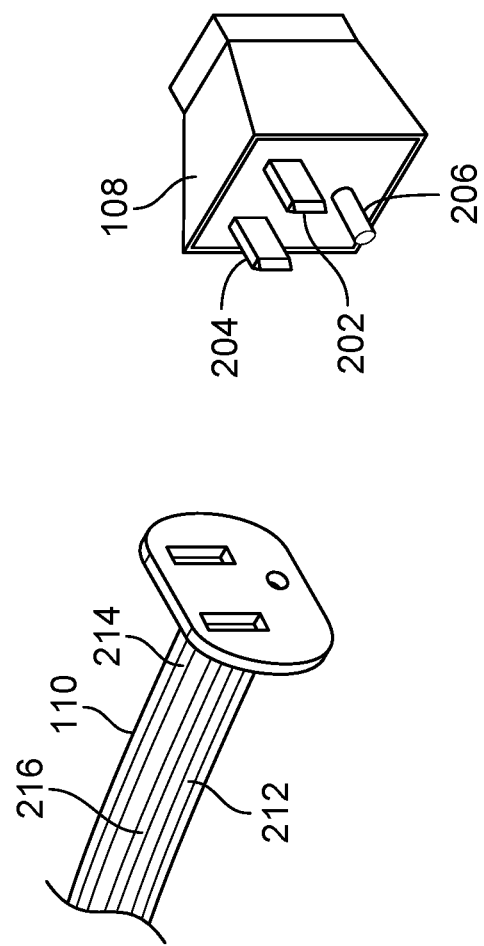
FIG. 2 shows an example of a socket on the hemodialysis machine to which a power supply cable is configured to connect.

FIG. 1B shows a back perspective view of the hemodialysis machine 100 that shows separate grounding connections for the power supply and the hydraulics system 104. The power supply (the majority of which is not shown) is configured to generally supply power to the components of the hemodialysis machine 100, including the blood circuit module 102 (e.g., including blood pumps), the hydraulics system 104 (e.g., including dialysate pumps), the touch screen 106, the processing module, various sensors, etc. The power supply includes a socket 108 that is configured to accept a power supply cable 110. The power supply cable 110 resides outside of the housing of the hemodialysis machine 100. The socket 108 includes a plurality of electrical conductors that are configured to mate with corresponding electrical connections (e.g., wires) in the power supply cable 110 when a first end of the power supply cable 110 is connected to the socket 108. The socket 108 is partially obscured by the power supply cable 110 in FIG. 1B due to the front view. Referring briefly to FIG. 2, examples of the socket 108 and the power supply cable 110 are shown. The socket 108 (shown in a perspective view) includes a line prong 202, a neutral prong 204, and a ground prong 206 (e.g., earth ground), and the power supply cable 110 includes a line wire 212, a neutral wire 214, and a ground wire 216 (e.g., earth ground). When the power supply cable 110 is plugged into the socket 108 of the hemodialysis machine 100, the wires 212, 214, 216 are electrically connected to the corresponding prongs 202, 204, 206 of the socket 108.

A second end of the power supply cable 110 is configured to plug into a power outlet. In some implementations, the second end of the power supply cable 110 may be part of a combined plug 130, as described in more detail below with respect to FIG. 3. In some implementations, the power outlet is a standard AC power outlet such as one that is standardized by the National Electrical Manufacturers Association (NEMA), such as a NEMA 5-15 grounded (Type B) outlet or a NEMA 5-20 outlet. The second end of the power supply cable 110 includes a line prong 112, a neutral prong 114, and a ground prong 116 (e.g., earth ground) that are electrically connected to the corresponding wires 212, 214, 216 of the power supply cable 110. The ground prong 116 and the ground wire (216 of FIG. 2) of the power supply cable 110 collectively form a first grounding connection of the hemodialysis machine 100 for grounding the power supply. When the second end of the power supply cable 110 is plugged into the power outlet, the prongs 112, 114, 116 of the power supply cable 110 are electrically connected to corresponding wires of the power outlet, as described in more detail below with respect to FIG. 3.

In addition to the first grounding connection (e.g., for grounding the power supply), the hemodialysis machine 100 includes a second grounding connection for the hydraulics system 104. The second grounding connection is separate from the grounding connection of the power supply and is configured to separately ground the components of the hydraulics system 104, including but not limited to the dialysate pumps.

The hemodialysis machine 100 includes a hydraulics grounding socket 118 that is configured to accept a hydraulics grounding cable 120. The hydraulics grounding cable 120 resides outside of the housing of the hemodialysis machine 100. The hydraulics grounding socket 118 includes an electrical conductor that is configured to mate with a corresponding electrical connection (e.g., a wire) in the hydraulics grounding cable 120 when a first end of the hydraulics grounding cable 120 is connected to the hydraulics grounding socket 118. A second end of the hydraulics grounding cable 120 is configured to plug into a ground orifice (e.g., earth ground) of a power outlet. In some implementations, the second end of the hydraulics grounding cable 120 may be part of the combined plug 130, as described in more detail below with respect to FIG. 3. In some implementations, the power outlet is a standard AC power outlet such as one that is standardized by NEMA, such as a NEMA 5-15 grounded (Type B) outlet or a NEMA 5-20 outlet. The second end of the hydraulics grounding cable 120 includes a ground prong 122 (e.g., earth ground) that is electrically connected to a corresponding ground wire (e.g., earth ground) (360 of FIG. 3) of the hydraulics grounding cable 120. The ground prong 122 and the ground wire 360 of the hydraulics grounding cable 120 collectively form the second grounding connection of the hemodialysis machine 100 for grounding the hydraulics system 104. When the second end of the hydraulics grounding cable 120 is plugged into the power outlet, the ground prong 122 of the hydraulics grounding cable 120 is electrically connected to a corresponding ground wire of the power outlet, as described in more detail below with respect to FIG. 3.

The hydraulics grounding socket 118 may be incorporated into a chassis of the hydraulics system 104. For example, the components of the hydraulics system 104 may be arranged in a chassis (e.g., a metal chassis), and the hydraulics grounding socket 118 may be electrically connected to the metal chassis (and, e.g., the electrical components of the hydraulics system 104). In this way, the second grounded connection provided at least in part by the hydraulics grounding cable 120 may provide a separate grounding connection for the electrical components of the hydraulics system 104 that is distinct from the grounding connection (e.g., the first grounding connection) of the power supply.

In some implementations, the locations on the hemodialysis machine 100 from where the first and second grounding connections emanate may be separated by a particular (e.g., predetermined) distance. In other words, the power supply cable 110 and the hydraulics grounding cable 120 may be electrically connected to the hemodialysis machine 100 at separate locations at the housing of the hemodialysis machine 100 that are separated by a particular distance. For example, the power supply socket 108 and the hydraulics grounding socket 118 may be separated by a predetermined distance of approximately 1-5 feet. In this way, the first and second grounding connections are spatially separated from each other outside of the housing of the hemodialysis machine 100 (e.g., due to the two distinct locations on the hemodialysis machine 100 from where the first and second grounding connections emanate). In some implementations, separation of the power supply socket 108 and the hydraulics grounding socket 118 may contribute to the separate and distinct nature of the two grounding connections.

Figure 3:
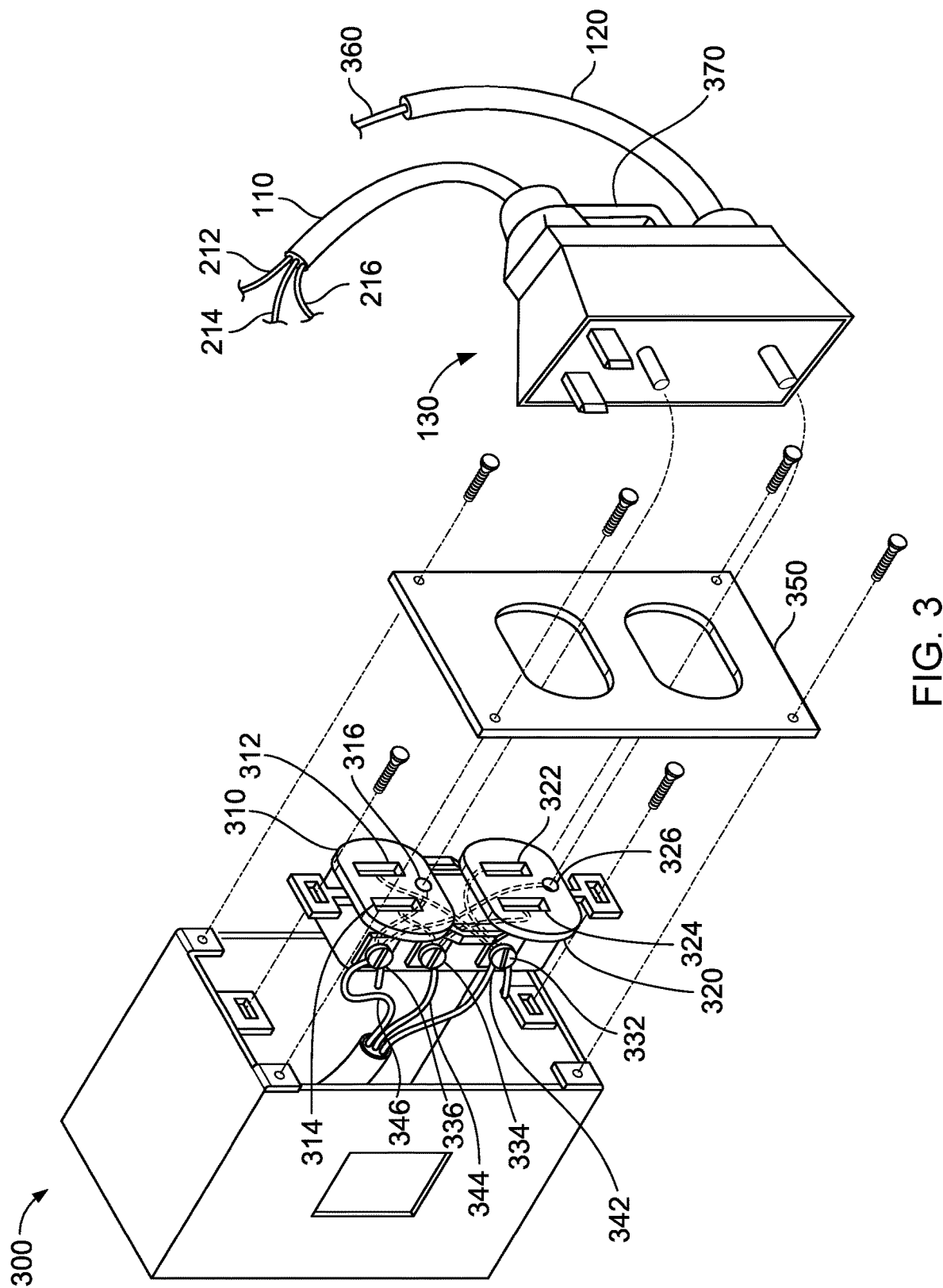
FIG. 3 shows an exploded view of an AC power outlet and a combined plug that is configured to be connected thereto.

FIG. 3 shows an exploded view of an AC power outlet 300 that is configured to electrically connect to the power supply cable 110 and the hydraulics grounding cable 120 (e.g., by accepting the prongs 112, 114, 116, 122 of the power supply cable 110 and the hydraulics grounding cable 120). The AC power outlet 300 includes a first AC socket 310 and a second AC socket 320 positioned beneath the first AC socket 310. The first AC socket 310 includes a line contact 312, a neutral contact 314, and a ground contact 316 (e.g., earth ground), and the second AC socket 320 includes a line contact 322, a neutral contact 324, and a ground contact 326 (e.g., earth ground). The AC power outlet 300 includes a line terminal 332 to which the line contacts 312, 322 are electrically connected (e.g., by wires shown in dotted lines), a neutral terminal 334 to which the neutral contacts 314, 324 are electrically connected (e.g., by wires shown in dotted lines), and a ground terminal 336 (e.g., earth ground) to which the ground contacts 316, 326 are electrically connected (e.g., by wires shown in dotted lines). A line wire 342 is connected to the line terminal 332, a neutral wire 344 is connected to the neutral terminal 334, and a ground wire 346 (e.g., earth ground) is connected to the ground terminal 336. The wires 342, 344, 346 may be connected, respectively, to a line bus, a neutral bus, and a ground bus (e.g., earth ground) of a power supply of the building in which the AC power outlet 300 resides.

The ground contact 316 of the first AC socket 310 and the ground contact 326 of the second AC socket 320 are electrically connected to the ground terminal 336 of the AC power outlet 300 by wires, shown as dotted lines in FIG. 3. Therefore, while the two ground contacts 316, 326 make up separate and distinct electrical connection points, the two ground contacts 316, 326 are electrically connected to each other at the ground terminal 336 behind a wall plate 350 of the AC power outlet 300. Nonetheless, because the two grounding connections (e.g., the first grounding connection formed by the ground prong 116 and the ground wire 216 of the power supply cable 110, and the second grounding connection formed by the ground prong 122 and the ground wire 360 of the hydraulics grounding cable 120) terminate at two different ground contacts 316, 326 of two different AC sockets 310, 320, the standards with which the hemodialysis machine 100 must comply (e.g., IEC 60364-7-710) are satisfied. For example, with respect to at least IEC 60364-7-710, there is no requirement for the two separate grounding connections to be connected to separate power outlets. In fact, connecting the two separate grounding connections to separate power outlets may have negative consequences (e.g., the creation of significant differences in current). Therefore, it may be advisable to connect both grounding connections to the same AC power outlet 300, albeit to different AC sockets 310, 320, assuming the wiring of the AC power outlet 300 is appropriately arranged.

In some implementations, the two grounding connections may be electrically connected within the dialysis machine 100 (e.g., via common paths through the chasses and/or shared electronic components). In some implementations, the separate grounding connections meeting in one common location (e.g., behind the wall plate 350 of the AC power outlet 300) can be beneficial because the common location has the same electrical potential (e.g., lower electrical potential) for each of the separate grounding connections to facilitate redundancy (e.g., complete redundancy) in the grounding connections.

In some implementations, the AC power outlet 300 may include a built-in fuse and/or a testing feature that can ensure the continued integrity of the electrical connection. For example, the AC power outlet 300 may include an indicator (e.g., a visual indicator in the form of a light) that is configured to provide an indication (e.g., by lighting and/or flashing the light) when one or both of the ground prong 122 of the hydraulics grounding cable 120 and the ground prong 116 of the power supply cable 110 are not connected to their respective ground contacts 316, 326. In some implementations, the ground prongs 116, 122 are longer than the line prong 112 and the neutral prong 114 to ensure proper grounding before electrical current enters the hemodialysis machine 100.

As briefly described above with respect to FIG. 1B, one or both of the second end of the power supply cable 110 and the second end of the hydraulics grounding cable 120 may be part of a single combined plug 130. The combined plug 130 is a single, contiguous structure that includes an upper portion and a lower portion. The upper portion corresponds to the power supply cable 110 and the lower portion corresponds to the hydraulics grounding cable 120. That is, the second end of the power supply cable 110, including the line prong 112, the neutral prong 114, and the ground prong 116, forms the upper portion of the combined plug 130, and the second end of the hydraulics grounding cable 120, including the ground prong 122, forms the lower portion of the combined plug 130.

The combined plug 130 also includes a handle 370 that is arranged substantially between the upper and lower portions. The handle 370 is configured to facilitate connection/disconnection of the combined plug 130 to/from the AC power outlet 300. An individual can simultaneously connect/disconnect all of the prongs 112, 114, 116, 122 of the combined plug 130 to/from the AC power outlet 300 in one motion by applying pressure to the handle 370. In some implementations, the combined plug 130 also includes a recess on a surface of the combined plug 130 that makes contact with the wall plate 350 when the combined plug 130 is connected to the AC power outlet 300. The recess allows a screw affixed to the wall plate 350 to fit therein such that the combined plug 130 can rest evenly against the wall plate 350 when the combined plug 130 is connected to the AC power outlet 300, thereby maintaining the integrity of the connection without disruption.

The combined plug 130 ensures that both grounding connections are concurrently made. For example, in implementations in which the power supply cable 110 and the hydraulics grounding cable 120 do not share a combined plug 130, an operator or technician may forget to plug the hydraulics grounding cable 120 into the second AC socket 320. Forgetting to connect the hydraulics grounding cable 120 may be more likely because the hemodialysis machine 100 may require only the power supply cable 110 to be connected in order to operate. In other words, the hemodialysis machine 100 may be able to operate (e.g., albeit potentially unsafely) without the hydraulics grounding cable 120 being connected. Therefore, including the second end of the power supply cable 110 and the second end of the hydraulics grounding cable 120 as a combined plug 130 may ensure that both the first grounding connection and the second grounding connection are made simultaneously and/or maintained concurrently.

The first grounding connection (e.g., formed by the ground prong 116 and the ground wire 216 of the power supply cable 110) is sometimes referred to as a standard grounding connection. In other words, the first grounding connection is provided by a ground prong and wire that is typically found in a standard AC power cable that also includes a line prong and a neutral prong. The second grounding connection (e.g., formed by the ground prong 122 and the ground wire 360 of the hydraulics grounding cable 120) is sometimes referred to as a non-standard grounding connection. In other words, the second grounding connection is provided by a ground prong that is typically not separately provided (e.g., without a corresponding line prong and neutral prong) in a cable that is to be connected to an AC socket. The second, non-standard grounding connection provides a solution to the leakage current concerns described above that is specifically tailored to help ensure safe operation of the hemodialysis machine 100.

Still referring to FIG. 3, the power supply cable 110 includes the line wire 212, the neutral wire 214, and the ground wire 216. Each of the wires 212, 214, 216 has its own insulation. All of the wires 212, 214, 216 are collectively enclosed within a common insulation, for example, the insulation of the power supply cable 110. The hydraulics grounding cable 120 includes the ground wire 360, which has its own insulation and which is also enclosed in the insulation of the hydraulics grounding cable 120.

As described above, the first and second grounding connections are separate and distinct in that they terminate at two different ground contacts 316, 326 of two different AC sockets 310, 320. The first and second grounding connections are also separate and distinct in that their respective ground wires 216, 360 are included within separate insulations (e.g., cables) and therefore do not share a common insulation. In other words, the first and second grounding connections are separate and distinct in that they are not included as part of a common cable (e.g., either the power supply cable 110 or the hydraulics grounding cable 120).

In some implementations, the second grounding connection terminates at the ground contact 326 of the second AC socket 320. In other words, the second grounding connection may provide grounding for the hydraulics system 104 of the hemodialysis machine 100 without providing a further electrical path to other portions of the hemodialysis machine 100 (or, e.g., to other devices). In some implementations, the second grounding connection is a power grounding connection (e.g., as opposed to a grounding connection for a non-powered line, such as a data line).

While certain implementations have been described, other implementations are possible.

Figure 4:
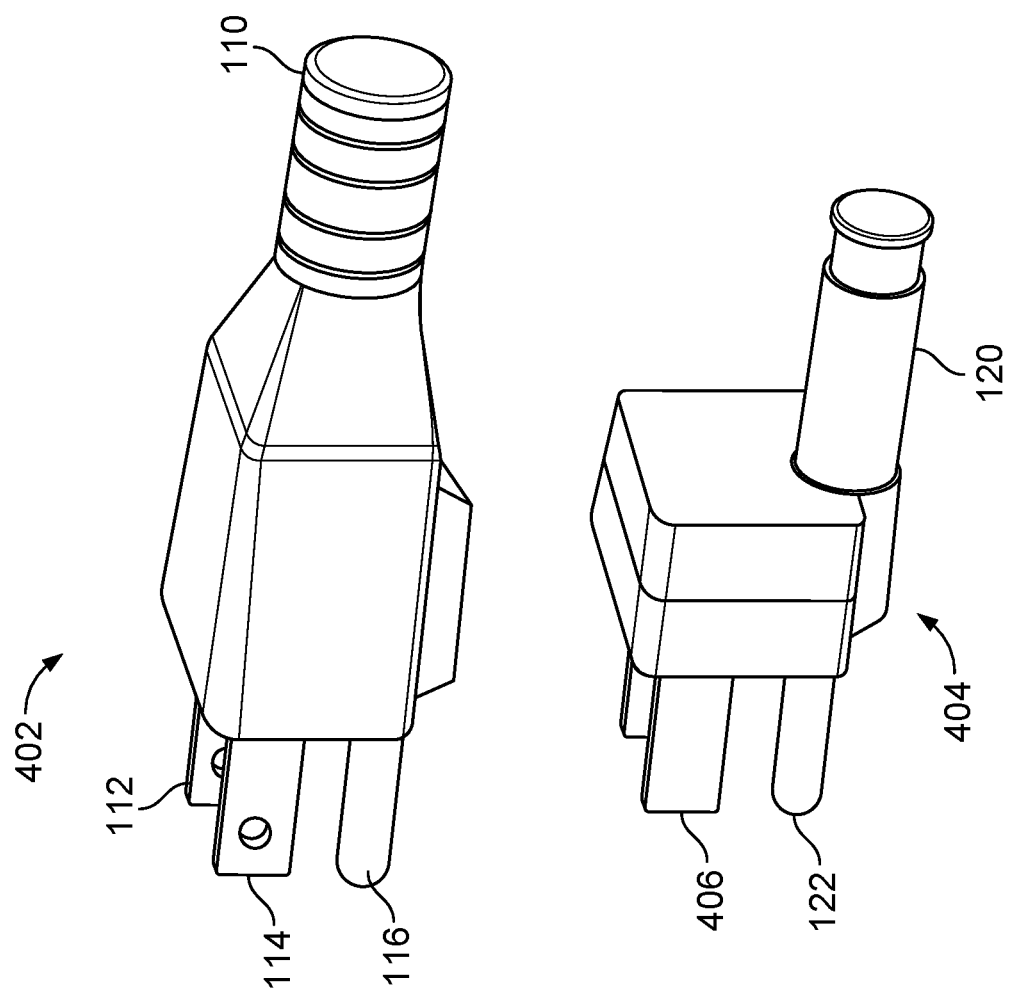
FIG. 4 shows an example of the power supply cable being separate from a hydraulics grounding cable.

While the power supply cable and the hydraulics grounding cable have been described as being part of a single combined plug, other configurations are possible. FIG. 4 shows an example in which the power supply cable 110 and the hydraulics grounding cable 120 are separate. That is, the second end of the power supply cable 110 includes a plug 402 and the second end of the hydraulics grounding cable 120 includes a separate plug 404. Each of the plugs 402, 404, is configured to separately plug into an AC socket. In this way, the ground prongs 116, 122 are included in separate plugs 402, 404.

In some implementations, providing separate plugs 402, 404 for the power supply cable 110 and the hydraulics grounding cable 120 allows the power supply cable 110 to be plugged into an AC socket that belongs to a first AC power outlet and the hydraulics grounding cable 120 to be plugged into an AC socket that belongs to a different (e.g., separate) AC power outlet. However, as described above, in some implementations, connecting the power supply cable 110 and the hydraulics grounding cable 120 to different AC power outlets may be undesirable in some cases.

In some implementations, the plug 404 of the hydraulics grounding cable 120 includes non-conductive prongs 406 for improving and/or ensuring the integrity of the connection between the plug 404 and the AC socket. In some implementations, the non-conductive prongs 406 are made of a polymer (e.g., plastic).

While the combined plug has been described as being a single contiguous structure (e.g., such that the second ends of the power supply cable and the hydraulics grounding cable are permanently connected to each other), in some implementations, the combined plug may be an adapter that is configured to combine the power supply cable and the hydraulics grounding cable. For example, the adapter may include an upper portion that corresponds to the power supply cable and a lower portion that corresponds to the hydraulics grounding cable. The upper portion may include a socket that includes a line contact, a neutral contact, and a ground contact (e.g., earth ground) that is configured to accept the prongs of the power supply cable. The socket may be arranged similar to that which is typically seen in a standard AC socket. The upper portion may also include a line prong, a neutral prong, and a ground prong (e.g., earth ground) that form electrical connections with the wires of the power supply cable when the power supply cable is plugged into the upper socket. Similarly, the lower portion may include a socket that includes a ground contact (e.g., earth ground) that is configured to accept the ground prong of the hydraulics grounding cable. The lower portion may also include a ground prong (e.g., earth ground) that forms an electrical connection with the ground wire of the hydraulics grounding cable when the hydraulics grounding cable is plugged into the lower socket. The prongs of the adapter may be plugged into an AC power outlet to provide power to the hemodialysis machine while ensuring proper grounding.

In some implementations, the adapter has a handle similar to that which is described above with respect to FIG. 3. Using an adapter as the combined plug (e.g., as opposed to the second ends of the power supply cable and the hydraulics grounding cable being permanently connected) can allow the cables to be disconnected for easier storage. Further, if one or more of the adapter, the power supply cable, and the hydraulics power cable are damaged, the damaged component can be replaced without requiring replacement of the other non-damaged components.

While the first grounding connection has been described as being collectively formed by the ground prong and the ground wire of the power supply cable, in some implementations, one or more portions of the first AC socket can also be considered part of the first grounding connection. For example, the ground contact of the first AC socket may be part of the first grounding connection. Similarly, while the second grounding connection has been described as being collectively formed by the ground prong and the ground wire of the hydraulics grounding cable, in some implementations, one or more portions of the second AC socket can also be considered part of the second grounding connection. For example, the ground contact of the second AC socket may be part of the second grounding connection.

While the hydraulics system has been described as including a balancing chamber, in some implementations, the hydraulics system does not include a balancing chamber. In some implementations, the hydraulics system may include one or more pumps for circulating dialysate through the dialysate circuit.

While the systems and techniques have been largely described with reference to a hemodialysis machine, other types of medical devices and medical treatment systems may also utilize the grounding techniques and devices described herein. Examples of other medical treatment systems that may employ the techniques described herein include peritoneal dialysis systems, hemofiltration systems, hemodiafiltration systems, apheresis systems, and cardiopulmonary bypass systems.

In some implementations, the medical device is a system that is configured for use with a patient for diagnostic and/or therapeutic purposes. The medical device may generally include two sets of components. In some examples, the medical device includes a first set of components that are configured to connect to and/or make contact with the patient, and a second set of components that are configured to facilitate other functionality of the medical device. Such a medical device may include multiple separate electrical grounding connections for each set of components.

The separate grounding connections may be substantially similar to the separate grounding connections described above with respect to FIGS. 1-4. For example, the medical device may include a power supply (e.g., for generally providing power to the medical device) that includes a first grounding connection, and a patient treatment system (e.g., that physically and/or electrically connects to the patient) that includes a separate, second grounding connection. The second, separate grounding connection may include a patient grounding cable that includes a ground wire (e.g., a separate ground wire than the ground wire of the power supply). The first grounding connection and the second grounding connection may include separate, distinct wires that each connects to a separate location at the medical device (e.g., at different locations at a housing of the medical device). The first and second grounding connections may terminate at respective grounds (e.g., earth grounds) of two separate AC power sockets. In some implementations, while the two grounding connections may be provided as separate, distinct wires (e.g., which may be enclosed within separate cabling), the two grounding connections may be incorporated as a single (e.g., combined) plug to ensure that both grounding connections are made substantially simultaneously and/or maintained concurrently.

Figure 5:
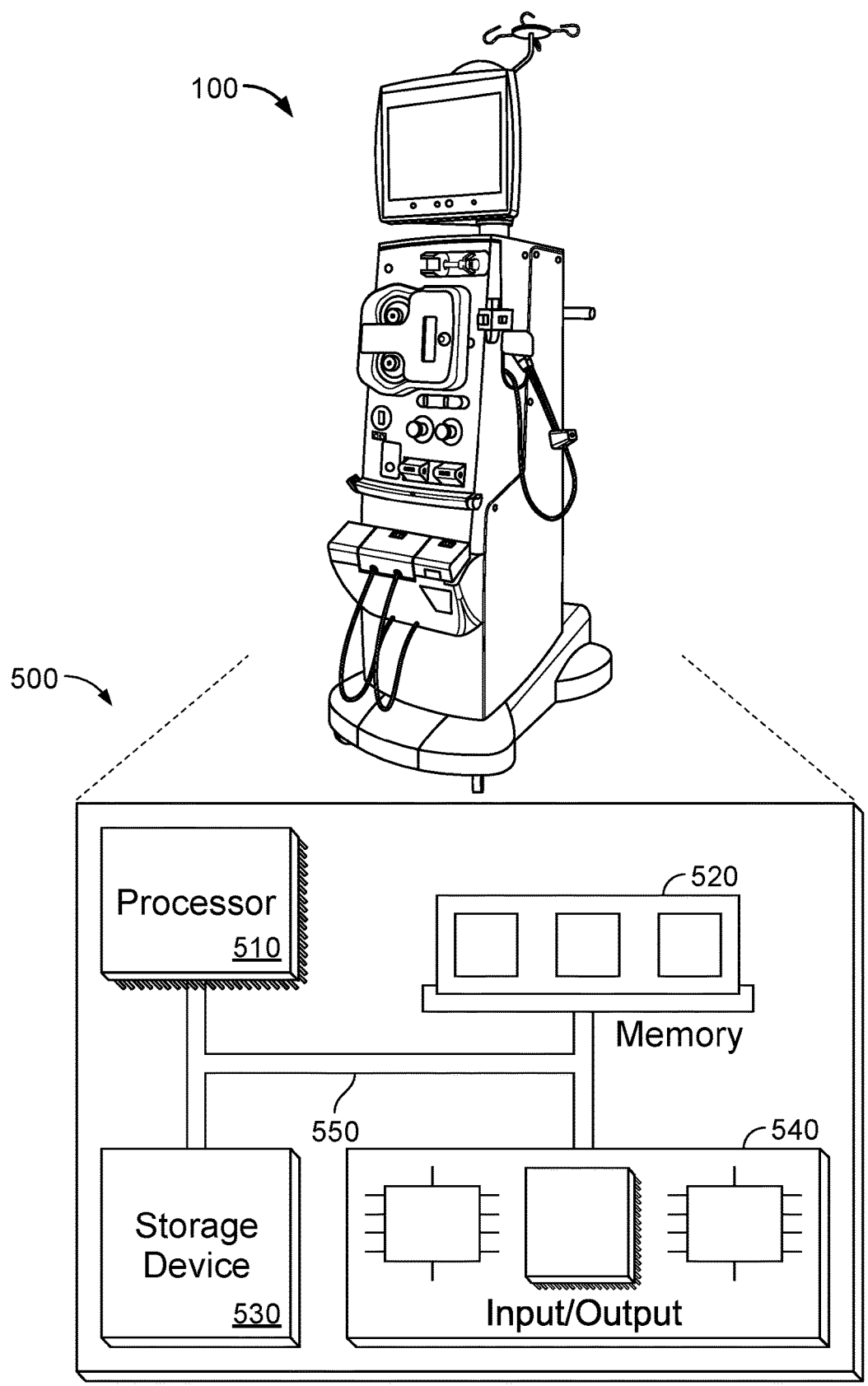
FIG. 5 is a block diagram of an example computer system.

FIG. 5 is a block diagram of an example computer system 500. For example, the processing module described with respect to FIG. 1A could be an example of the system 500 described here. The system 500 includes a processor 510, a memory 520, a storage device 530, and an input/output device 540. Each of the components 510, 520, 530, and 540 can be interconnected, for example, using a system bus 550. The processor 510 is capable of processing instructions for execution within the system 500. The processor 510 can be a single-threaded processor, a multi-threaded processor, or a quantum computer. The processor 510 is capable of processing instructions stored in the memory 520 or on the storage device 530. The processor 510 may execute operations such as causing the dialysis system to carry out functions related to a dialysis treatment.

The memory 520 stores information within the system 500. In some implementations, the memory 520 is a computer-readable medium. The memory 520 can, for example, be a volatile memory unit or a non-volatile memory unit. In some implementations, the memory 520 stores information related to a treatment to be administered to a patient.

The storage device 530 is capable of providing mass storage for the system 500. In some implementations, the storage device 530 is a non-transitory computer-readable medium. The storage device 530 can include, for example, a hard disk device, an optical disk device, a solid-date drive, a flash drive, magnetic tape, or some other large capacity storage device. The storage device 530 may alternatively be a cloud storage device, e.g., a logical storage device including multiple physical storage devices distributed on a network and accessed using a network. In some implementations, the information stored on the memory 520 can also or instead be stored on the storage device 530.

The input/output device 540 provides input/output operations for the system 500. In some implementations, the input/output device 540 includes one or more of network interface devices (e.g., an Ethernet card), a serial communication device (e.g., an RS-232 port), and/or a wireless interface device (e.g., a short-range wireless communication device, an 802.11 card, a 3G wireless modem, or a 4G wireless modem). In some implementations, the input/output device 540 includes driver devices configured to receive input data and send output data to other input/output devices, e.g., a keyboard, a printer, and display devices (such as the touch screen 106). In some implementations, mobile computing devices, mobile communication devices, and other devices are used.

In some implementations, the system 500 is a microcontroller. A microcontroller is a device that contains multiple elements of a computer system in a single electronics package. For example, the single electronics package could contain the processor 510, the memory 520, the storage device 530, and input/output devices 540.

Although an example processing system has been described in FIG. 5, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of implementations of the invention have been described. Nevertheless, it will be understood that various modifications may be made without departing from the spirit and scope of the invention. Accordingly, other implementations are within the scope of the following claims.

What is claimed is:

1. A plug that is configured to plug into an AC power outlet, the plug comprising:
    a power supply cable that includes a first ground wire electrically connected to a first ground prong of the plug, the power supply cable for providing power to a medical device; and
    a grounding cable for providing a grounding connection to a treatment system of the medical device, the grounding cable including a second ground wire electrically connected to a second ground prong of the plug, wherein the treatment system is configured to physically or electrically connect to a patient.

2. The plug of claim 1, wherein the first ground prong and the first ground wire are electrically isolated from the second ground prong and the second ground wire.

3. The plug of claim 1, wherein the first ground wire and the second ground wire do not share a common insulation.

4. The plug of claim 1, wherein an adapter is configured to:
    removably connect to and from an electrical connection with the power supply cable;
    removably connect to and from an electrical connection with the grounding cable; and
    plug into the AC power outlet.

5. The plug of claim 1, further comprising a handle for facilitating simultaneous connection or disconnection of the power supply cable and the grounding cable to or from the AC power outlet.

6. The plug of claim 5, wherein a first end of the handle connects to the plug near a connected end of the power supply cable and a second end of the handle connects to the plug near a connected end of the grounding cable.

7. The plug of claim 1, wherein the grounding connection of the treatment system is separate and distinct from the first ground wire and the first ground prong of the power supply cable.

8. The plug of claim 1, further comprising:
a line prong that is electrically connected to a line wire of the power supply cable; and
a neutral prong that is electrically connected to a neutral wire of the power supply cable.

9. The plug of claim 1, wherein the first ground prong and the first ground wire are in electrical communication with the second ground prong and the second ground wire via a connection that occurs behind a wall plate of the AC power outlet when the plug is plugged into the AC power outlet.

10. The plug of claim 1, wherein the plug is a contiguous piece of material to which all prongs are connected.

11. The plug of claim 1, further comprising one or more non-conductive prongs for improving an integrity of a connection between the plug and the AC power outlet.

12. The plug of claim 1, wherein the plug is configured such that the medical device complies with one or more requirements specified by a standards organization when the first ground prong is connected to a first AC socket of the AC power outlet and the second ground prong is connected to a second AC socket of the AC power outlet.

13. The plug of claim 12, wherein the standards organization is the International Electrotechnical Commission (IEC) and the one or more requirements are specified in IEC 60364-7-710.

14. The plug of claim 1, wherein the grounding cable is configured to plug into a grounding socket of the medical device.

15. The plug of claim 14, wherein the grounding socket is in electrical communication with a metal chassis of the treatment system.

16. The plug of claim 1, wherein the medical device is a dialysis machine.

17. The plug of claim 1, wherein the power supply cable and the grounding cable electrically connect to the medical device at separate locations at a housing of the medical device.

18. The plug of claim 1, further comprising one or more recesses sized to allow screws of a wall plate connected to the AC power outlet to fit therein such that the plug rests evenly against the wall plate when connected to the AC power outlet.

19. The plug of claim 1, wherein the plug ensures that two grounding connections are made simultaneously and maintained concurrently when the plug is plugged into the AC power outlet.

\* \* \* \* \*